(12) United States Patent
Chevallet et al.

(10) Patent No.: US 7,540,958 B2
(45) Date of Patent: Jun. 2, 2009

(54) DEVICE FOR CONTROLLING BLOOD CIRCULATION FOR A SINGLE NEEDLE CIRCUIT

(75) Inventors: Jacques Chevallet, Serezin du Rhone (FR); Jean-Louis Romarie, Decines Charpieu (FR); Alain Frugier, Tignieu (FR)

(73) Assignee: Gambro Lundia AB (SE)

( * ) Notice: Subject to any disclaimer, the term of this patent is extended or adjusted under 35 U.S.C. 154(b) by 703 days.

(21) Appl. No.: 11/074,067

(22) Filed: Mar. 8, 2005

(65) Prior Publication Data

US 2005/0205476 A1    Sep. 22, 2005

Related U.S. Application Data

(60) Provisional application No. 60/558,125, filed on Apr. 1, 2004.

(30) Foreign Application Priority Data

Mar. 8, 2004    (FR)    .................................. 04 02381

(51) Int. Cl.
*B01D 61/28* (2006.01)
*B01D 61/18* (2006.01)

(52) U.S. Cl. ........................... 210/258; 210/85; 210/86; 210/87; 210/90; 210/96.1; 210/97; 210/102; 210/103; 210/104; 210/252; 210/257.2; 210/321.6; 210/645; 210/646; 210/650; 604/5.01; 604/65; 604/67

(58) Field of Classification Search ................. 210/645, 210/646, 650, 85, 86, 87, 90, 96.1, 97, 102, 210/103, 104, 143, 188, 252, 257.2, 258, 210/321.6; 604/5.01, 65, 67
See application file for complete search history.

(56) References Cited

U.S. PATENT DOCUMENTS 4,758,336 A    7/1988    Bock et al.

(Continued)

FOREIGN PATENT DOCUMENTS

DE    37 20 664 A1    1/1989

(Continued)

OTHER PUBLICATIONS

International Preliminary Report on Patentability of International Application No. PCT/IB2005/000468.

*Primary Examiner*—John Kim
(74) *Attorney, Agent, or Firm*—Finnegan, Henderson, Farabow, Garrett & Dunner L.L.P.

(57) ABSTRACT

Device for extracorporeal treatment of blood 1 intended to operate in a mode with a single needle 2, comprising:
   a treatment unit 3 having a first compartment 4 and a second compartment 5, which are separated by a semi-permeable membrane 6,
   an extracorporeal blood circuit comprising a single needle 2, an intake line 7 in fluid communication with the first compartment 4 of the treatment unit 3, the first compartment 4, and a return line 8 in fluid communication with the first compartment 4 of the treatment unit 3,
   a purge line 9 at the outlet of the second compartment 5,
   a closure means (10, 11) acting on at least the intake line 7 and the return line 8 in order to generate the alternate sequence of blood intake and return,
   at least a first chamber 12 which is in fluid communication with the extracorporeal blood circuit and defines a first additional blood volume, the first chamber 12 having a variable total content;
   the first chamber 4 being rigid and including at least one wall capable of being moved,
   the device including a means 19 acting on the chamber 12 in order to modify the volume of the chamber 12, making it possible to store blood during the arterial phase and release blood during the venous phase.

35 Claims, 15 Drawing Sheets

U.S. PATENT DOCUMENTS

| | | | |
|---|---|---|---|
| 4,940,455 A | | 7/1990 | Guinn |
| 5,015,226 A | * | 5/1991 | Polaschegg ................ 604/6.12 |
| 5,227,049 A | * | 7/1993 | Chevallet et al. .............. 210/97 |
| 5,318,511 A | * | 6/1994 | Riquier et al. ............. 604/6.05 |
| 5,910,252 A | * | 6/1999 | Truitt et al. ................. 210/645 |
| 6,645,166 B2 | * | 11/2003 | Scheunert et al. ......... 604/6.11 |

FOREIGN PATENT DOCUMENTS

| | | |
|---|---|---|
| EP | 0 071 951 B1 | 2/1983 |
| EP | 0 392 304 A1 | 10/1990 |
| EP | 0 462 422 B1 | 12/1991 |
| EP | 1 184 046 A1 | 3/2002 |
| FR | 2 548 906 | 1/1985 |
| FR | 2 632 360 | 12/1989 |
| FR | 2 672 217 | 8/1992 |
| FR | 2 672 219 | 8/1992 |
| WO | WO 01/08557 A1 | 2/2001 |

* cited by examiner

STATE OF THE ART

FIG 2 STATE OF THE ART

STATE OF THE ART

STATE OF THE ART

STATE OF THE ART

STATE OF THE ART

Invention — 1st embodiment

Invention – 1st embodiment

Invention – 2nd embodiment

Invention – 3rd embodiment

Invention – 4th embodiment

Invention — 4th embodiment

FIG 13 arterial phase

Invention — 4th embodiment

DEVICE FOR CONTROLLING BLOOD CIRCULATION FOR A SINGLE NEEDLE CIRCUIT

CROSS REFERENCE TO RELATED APPLICATIONS

This application claims priority of French patent application N°0402381, filed on Mar. 8, 2004 and the benefit of U.S. Provisional Application No. 60/558,125, filed on Apr. 1, 2004, the contents of which are incorporated herein by reference.

TECHNICAL FIELD OF THE INVENTION

The present invention relates to a device for extracorporeal treatment of blood intended to be connected to a patient by means of a single needle, this device being for example an artificial kidney or a plasmapheresis device.

PRIOR ART

With such devices, it is known to carry out the connection of the extracorporeal blood circuit to the patient by two modes of operation: the "double-needle" mode and the "single needle" mode. In the double-needle mode, two needles are used: a first for the patient's arterial access, that is to say for taking the blood from the patient, and a second needle for the patient's blood access, that is to say for returning the blood into the patient. The blood thus flows in a circuit through which it passes entirely in one direction: first needle, arterial line, then blood compartment of the filter, then venous line, and finally second needle. This mode of operation makes it possible to take the blood and give it back simultaneously. However, this mode makes it necessary to insert two needles into the patient, for example in the patient's fistula. This double-needle mode is used very widely to obtain good efficiency but it has its limitations, in particular owing to the patient. This is because with successive treatments, at a rate of three sessions per week in the case of a chronic treatment, the patient's fistula may suffer damage and no longer permit advantageous insertion. A small fistula may prevent access for both needles, or may then entail insertion of two needles so close to each other that an excessive recirculation phenomenon would reduce the quality of the treatment. By necessity and/or in order to avoid increasing the fragility of the patient's vascular access, therefore, the "single needle" mode may be opted for.

In the single-needle mode, a single needle is inserted into the patient, for example into his or her fistula. There are therefore two separate and alternating phases of operation.

The first phase is referred to as the arterial phase, during which the blood is taken from the patient via the single needle into the extracorporeal circuit, and the second phase is referred to as the venous phase, during which the blood is passed from the extracorporeal blood circuit back to the patient through the single needle. Owing to the use of a single needle, the flow of the blood throughout the extracorporeal circuit, including the needle, is not continuous and a certain volume of blood (referred to as the "stroke volume") has to be stored in the extracorporeal circuit during each cycle of operation. Problems therefore arise concerning the quality and quantity of blood treatment in relation to the session time.

A plurality of single-needle circuits have been proposed.

A first known circuit is schematically represented in FIG. 1. The extracorporeal circuit 1 has two clamps, AC (arterial clamp 10) and VC (venous clamp 11), an arterial pump 14, and an expansion chamber 50 with a fixed volume to store the blood being treated. In an arterial phase, the patient's blood flows through the arterial line 7 and enters the treatment unit 3 then the venous line 8. Since the blood cannot be re-injected because the clamp 11 (VC) is closed, it is stored in the expansion chamber 50 in fluid communication with the venous line 8. The capacity of the expansion chamber 50 is constant in volume, it contains only air before operation, and the volume of blood stored during operation increases and decreases alternately. The pressure in the chamber will be such that the product Volume×Pressure of blood remains constant. The greater the fluctuation in volume is, therefore, the greater will be that of the pressure, which is not desirable. It is therefore known to add a "dead volume" to the chamber, that is to say a volume of air added to that of the chamber by a second chamber 51 in air communication with the first chamber 50, in order to minimize the variations in volume and pressure inside the chamber 50.

Although the circuit is indeed simple, the blood flow rate in the dialyzer (or treatment unit) is not continuous, the arterial pump 14 does not operate continuously and the venous phase is not optimized because the flow rate in the needle is dictated by the pressure in the chamber. The problem of haemocompatibility furthermore arises, all the more so because of the expansion chamber 50 in which the surface of the air/blood interface entails coagulation problems.

A second known circuit, proposed in FIG. 2, is an improvement of the previous circuit. In order to obtain a continuous flow rate of blood in the dialyzer 3, the extracorporeal circuit which is schematically represented includes a second expansion chamber 60 connected to a second dead volume 61, for storing the blood. This allows the blood to pass continuously through the dialyser and increases the quality of dialysis treatment. It is, however, necessary for the volume in each of the two expansion chambers to be regulated correctly, so that it is identical and equal to half of the stroke volume: this fairly intricate operation is carried out by an operator. Other drawbacks remain: the fluctuating pressure of the blood, the non-optimized venous phase, the problem of haemocompatibility and coagulation of the blood.

A third circuit is known and, in FIG. 3, represents an improvement of the circuit in FIG. 2. The difference from the second circuit is the position of the arterial pump 14, which is connected downstream of the expansion chamber 60 placed on the arterial line 7, delivering a constant flow rate in the dialyser 3. In general, the other drawbacks remain: the intake and delivery pressures vary during the arterial and venous phases, the fluctuating pressure of the blood, the problem of haemocompatibility and coagulation of the blood.

Next, with reference to FIG. 4, a second pump 52 has been added downstream of the expansion chamber 50 placed on the venous line, and a bubble trap 53 has been added downstream of the second pump 52 but upstream of the venous clamp 11. This has made it possible to optimize the venous phase, because the flow rate is no longer dictated by the pressure of the expansion chamber 50. The haemocompatibility and the undesired coagulation remained problems, however, besides a circuit which has been made more complex.

Moreover, another problem to be dealt with is the regulation and control of such a device. In fact, an operator has to intervene for priming the circuit and regulating the expansion chambers 50 and 60. This requires the constant presence of staff with the patient, and precise and skilful intervention by these staff. There has been a desire to auto-regulate the operation of such machines.

A circuit 1 with a single needle 2, disclosed in Patent FR 2 584 906 (cited here by way of reference), is known and is illustrated in FIG. 5. It includes an arterial pump 14 and two expansion chambers, arterial 50 and venous 60, for storing the blood. In order to auto-regulate the operation of the device, a high limit detector 54 (respectively a low limit detector 55) are connected onto the venous expansion chamber 50 for detecting a maximum (respectively minimum) quantity of blood being treated. The detected signals are used for control of the arterial and venous phases by a calculation and control unit 15. The limit detector includes a pressure value detector for the volume of air contained in each reservoir. The control procedure nevertheless remains intricate, and the problem of haemocompatibility still arises.

Lastly, it is an object of the invention to which Patent FR 2 672 217 (cited here by way of reference) relates, and which is illustrated in FIG. 6, to auto-regulate a device 1 having a single needle 2. In the flow direction of the blood, the circuit 1 includes an arterial clamp 10, an arterial pump 14, an arterial expansion chamber 60, a treatment unit 3, a venous expansion chamber 50 and a venous pump 52. Each expansion chamber (50, 60) is connected to pressure regulating means (56 and 66) for maintaining an adjustable, substantially constant pressure in the chamber. The regulating means are pumps, which are controlled in order to take air in during an arterial phase, and which are controlled in order to the deliver air during a venous phase, the purpose of this being to maintain a constant pressure on either side of the filter 3 and to set a constant pressure inside the filter.

Another improvement has been proposed in Patent Application EP0392304, which relates to a single-needle dialysis machine including at least one blood container in the form of a flexible bag arranged between two support plates. One of the plates is fixed and the other can be moved, during the venous phase only, in order to control the emptying of the flexible bag. During the arterial phase, the bag becomes filled up to a certain high liquid limit and acts on the free mobile plate. During the venous phase, the bag is emptied by the pressure exerted by the controlled mobile plate on the entirely flexible bag, until a low liquid level is reached. The high and low pressure limits are detected by a pressure detector in the bag. This device uses a flexible bag for holding blood and air, but it nevertheless has the problem of haemocompatibility.

Another proposal is found in Patent Application EP0462422, which discloses a device with at least one blood accumulator which, at least in the venous phase, is supplied with a force produced by an external instrument, so that a pressure essentially independent of its filled volume is formed on the inside. The accumulator is therefore inflated like a balloon during the arterial phase, and deflated during the venous phase.

In this embodiment, the management of flow rate and pressure with a deformable flexible bag remains very difficult and not very accurate, especially as the pressure also turns out to be dependent on the elasticity of the bag.

Recurrent problems have thus been encountered for many years when producing the single-needle extracorporeal blood treatment devices of the prior art. These circuits are complex and expensive owing to the number of expansion chambers, pumps and bubble traps which are used, etc., and they are not very efficient in terms of the maximum blood flow which circulates and is therefore treated. Problems of haemocompatibility and coagulation, in particular owing to the air/blood interface in each reservoir, are still observed.

The problem of constant haemodynamic conditions also arises: the flow rate and pressure of blood, in particular, ought to be as constant as possible. It is furthermore desirable to regulate or auto-regulate the operation of the machine, without systematic intervention by an operator during the treatment session.

These circuits are furthermore reserved for use in a single-needle mode, and cannot be used in a double-needle mode, particularly in the field of renal intensive care.

It is an object of the present application to provide a single-needle extracorporeal blood treatment device which is designed in a simple way, can be used in a device for the double-needle mode, is reliable, can be regulated and entails less coagulation. It is also an object to improve the haemodynamic conditions in order to obtain substantially constant blood flow rates and pressures.

DESCRIPTION OF THE INVENTION

In order to achieve these objects, the invention provides an extracorporeal blood treatment device 1 (FIG. 7) intended to operate in a mode with a single needle 2, comprising:

a treatment unit 3 having a first compartment 4 and a second compartment 5, which are separated by a semipermeable membrane 6, an extracorporeal blood circuit comprising a single needle 2, an intake line 7 in fluid communication with the first compartment 4 of the treatment unit 3, the first compartment 4, and a return line 8 in fluid communication with the first compartment 4 of the treatment unit 3, a purge line 9 at the outlet of the second compartment 5, a closure means (10, 11) acting on at least the intake line 7 and the return line 8 in order to generate the alternate sequence of blood intake and return, at least a first chamber 12 which is in fluid communication with the extracorporeal blood circuit and defines a first additional blood volume, the first chamber 12 having a variable total content, the first chamber being rigid and including at least one wall capable of being moved, the device including a means 19 acting on the chamber 12 in order to modify the volume of the chamber 12, making it possible to store blood during the arterial phase and release blood during the venous phase.

The invention also relates to a disposable device 100 (FIG. 8) for use in an extracorporeal blood circuit 1 with a single needle 2, comprising:

a treatment unit 3 having a first compartment 4 and a second compartment 5, which are separated by a semipermeable membrane 6, an extracorporeal blood circuit comprising a single needle 2, an intake line 7, the first compartment 4 of the treatment unit 3 and a return line 8, at least a first chamber 12 for defining a first additional blood volume which includes a connection 22 in fluid communication with the intake line 7 or with the return line 8, the first chamber 12 having a variable total content, the first chamber 12 being rigid and including at least one wall capable of being moved.

Lastly, the invention relates to an extracorporeal blood treatment method for implementing the extracorporeal blood treatment device according to the invention.

Other advantages and characteristics of the invention will become apparent on reading the description which follows.

BRIEF DESCRIPTION OF THE DRAWINGS

Reference will be made to the appended drawings, in which:

FIGS. 1 to 6 were discussed in the introduction to the prior art.

DETAILED DESCRIPTION OF EMBODIMENTS OF THE INVENTION

Figure 1:
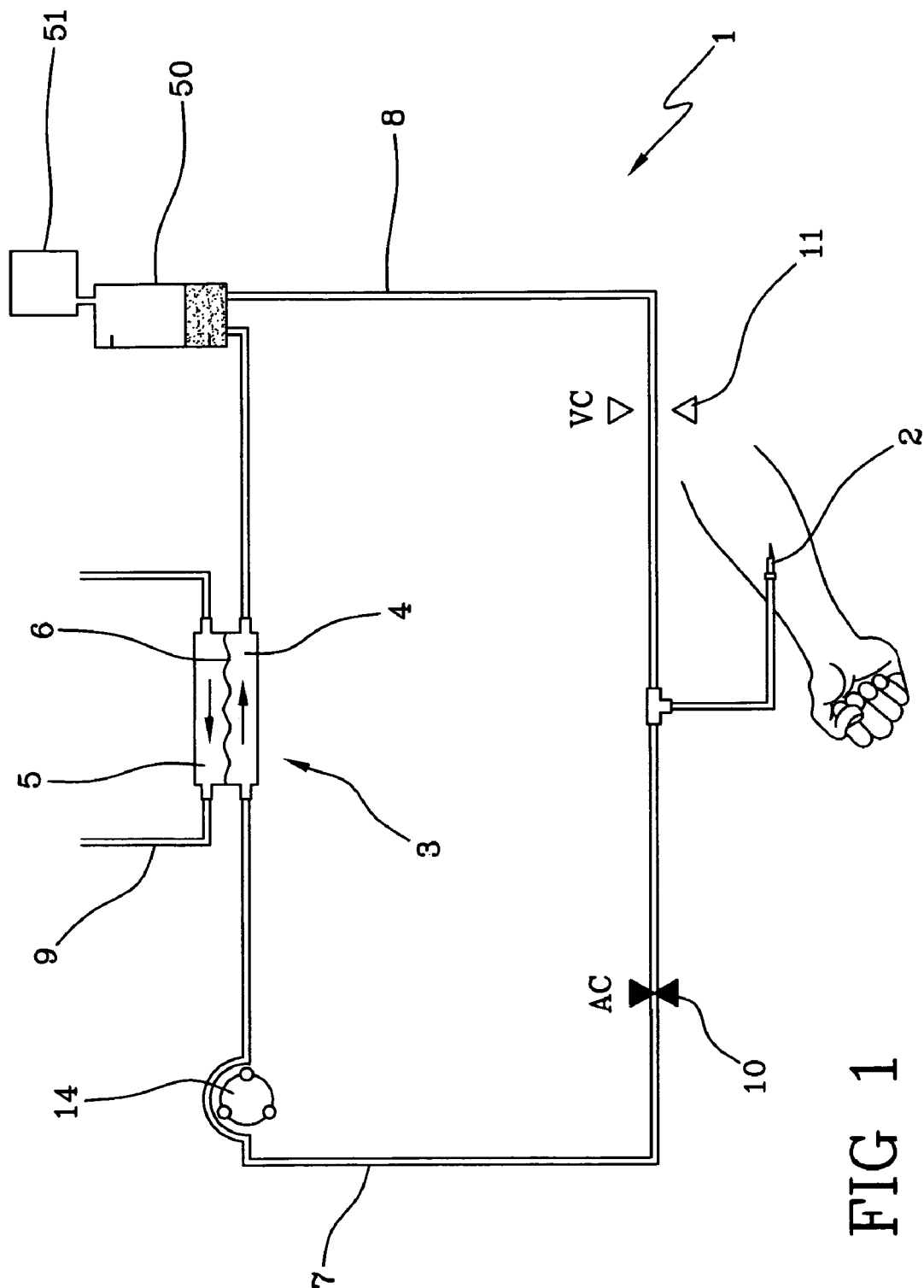
FIGS. 1 to 4 represent prior-art circuits relating to the treatment of blood with a single-needle device.
Figure 2:
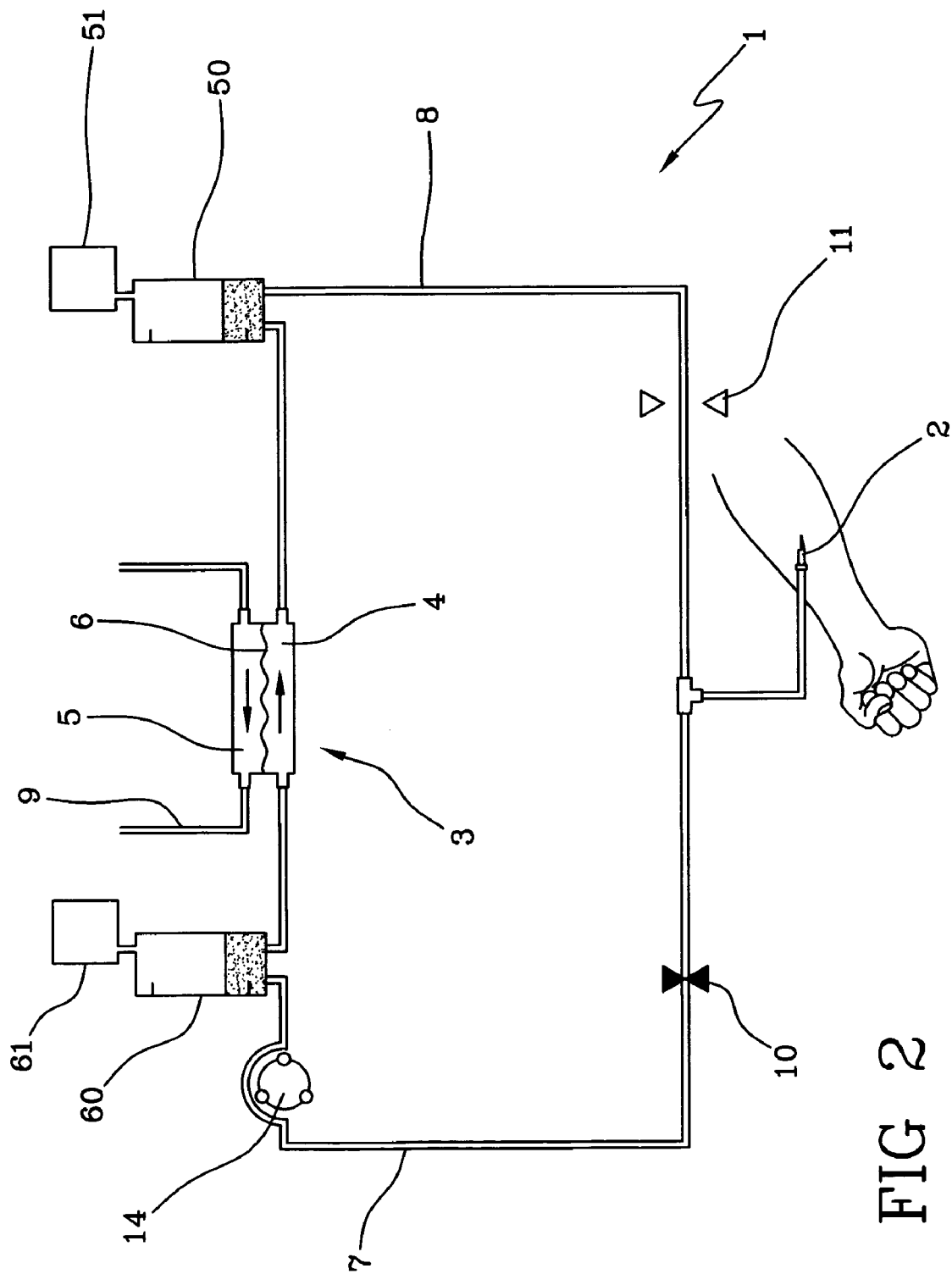
Figure 3:
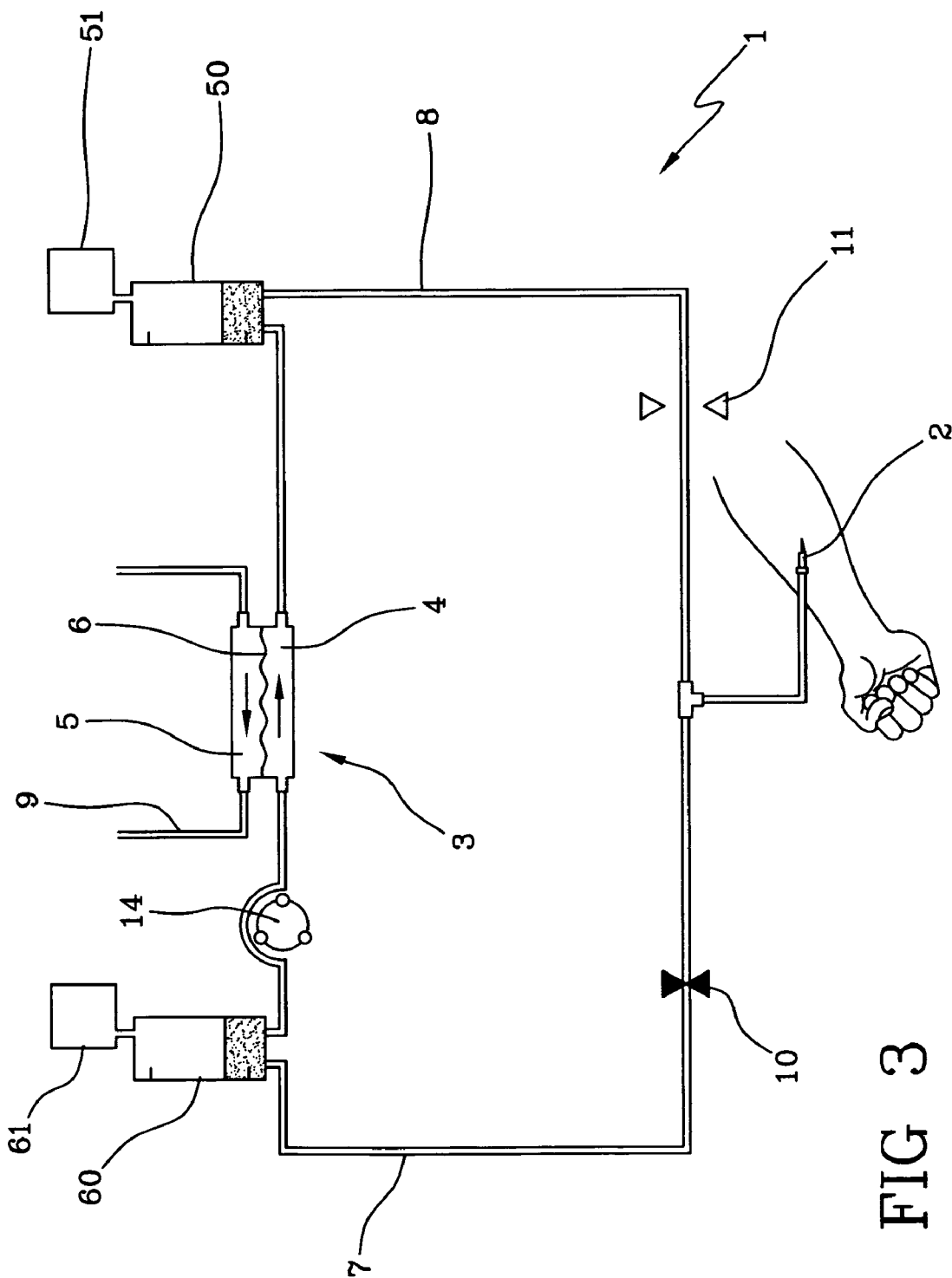
Figure 4:
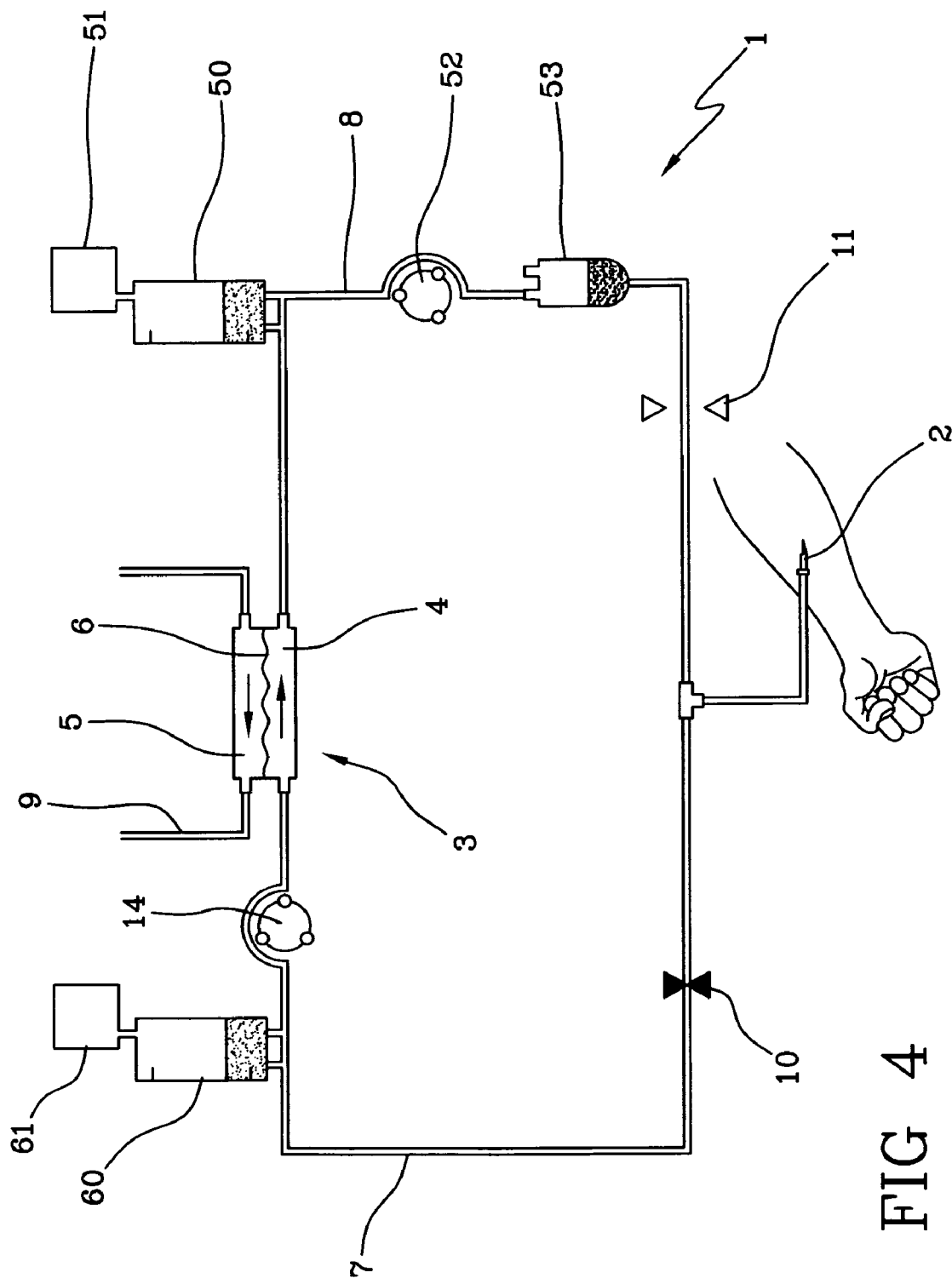
Figure 5:
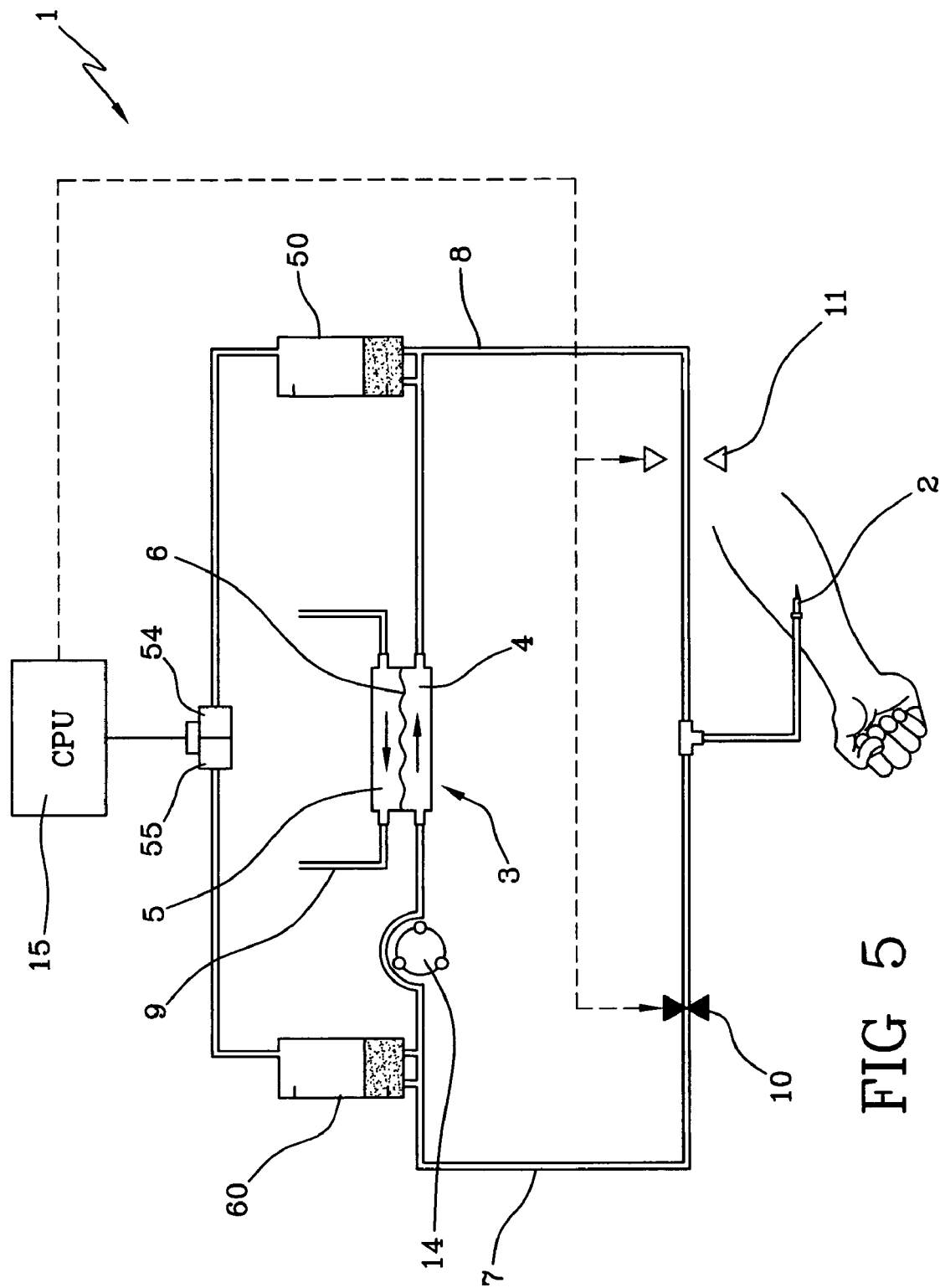
FIG. 5 represents the prior art described in Patent FR 2 548 906.
Figure 6:
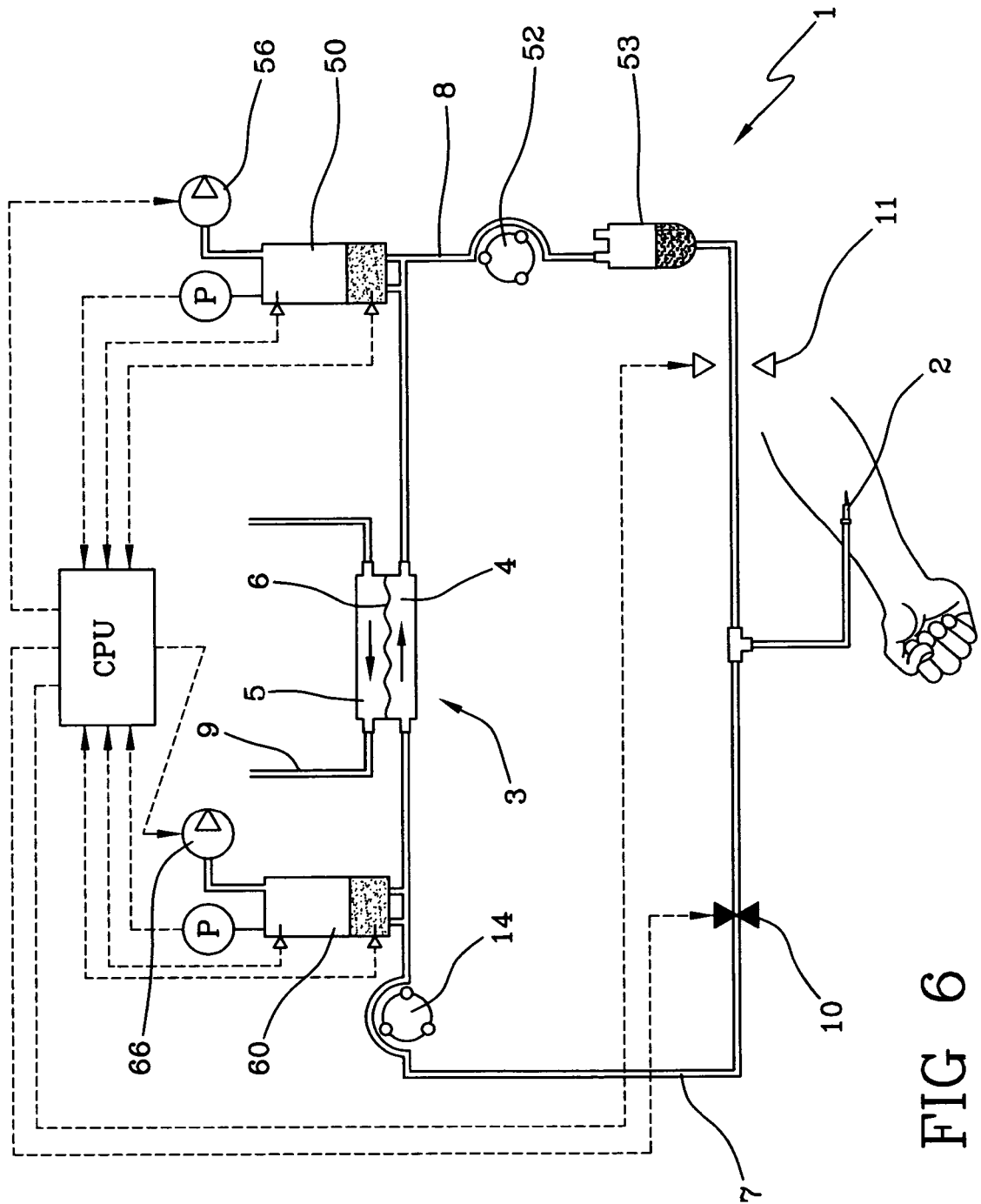
FIG. 6 represents the prior art described in Patent FR 2 672 217.
Figure 7:
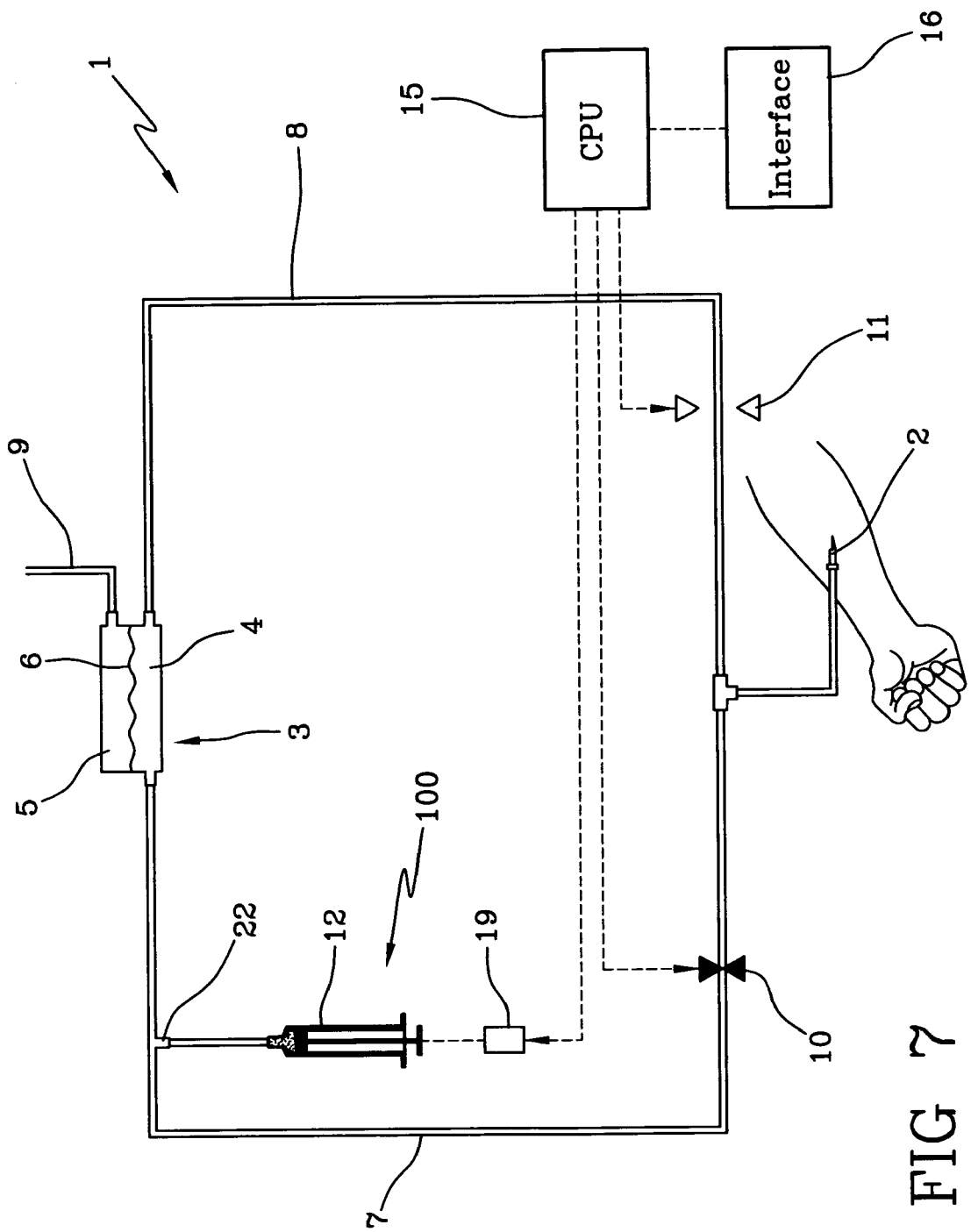
FIG. 7 (respectively FIG. 8) represents in a schematized way a first embodiment (respectively the corresponding disposable device) of the invention with one chamber.

FIG. 7 represents an extracorporeal blood treatment device 1 intended to operate in a mode with a single needle 2, comprising a treatment unit 3 having a first compartment 4 and a second compartment 5, which are separated by a semipermeable membrane 6, an extracorporeal blood circuit comprising a single needle 2, an intake line 7 in fluid communication with the first compartment 4 of the treatment unit 3, the first compartment 4, and a return line 8 in fluid communication with the first compartment 4 of the treatment unit 3, a purge line 9 at the outlet of the second compartment 5, a closure means (10, 11) acting on at least the intake line 7 and the return line 8 in order to generate the alternate sequence of blood intake and return, at least a first chamber 12 which is in fluid communication with the extracorporeal blood circuit and defines a first additional blood volume; the first chamber 12 having a variable total content, being rigid and including at least one wall capable of being moved; the device including a means 19 acting on the chamber 12 in order to modify the volume of the chamber 12. The chamber 12 will thus store blood during the arterial phase and release blood during the venous phase.

The chamber is rigid in so far as it can withstand the deformation forces liable to be induced by a pressure, in particular. The material could be plastic, glass, etc.

In this first embodiment, the first chamber 12 is in fluid communication with the intake line 7.

As an alternative, the first chamber 12 is in fluid communication with the return line 8.

Figure 9:
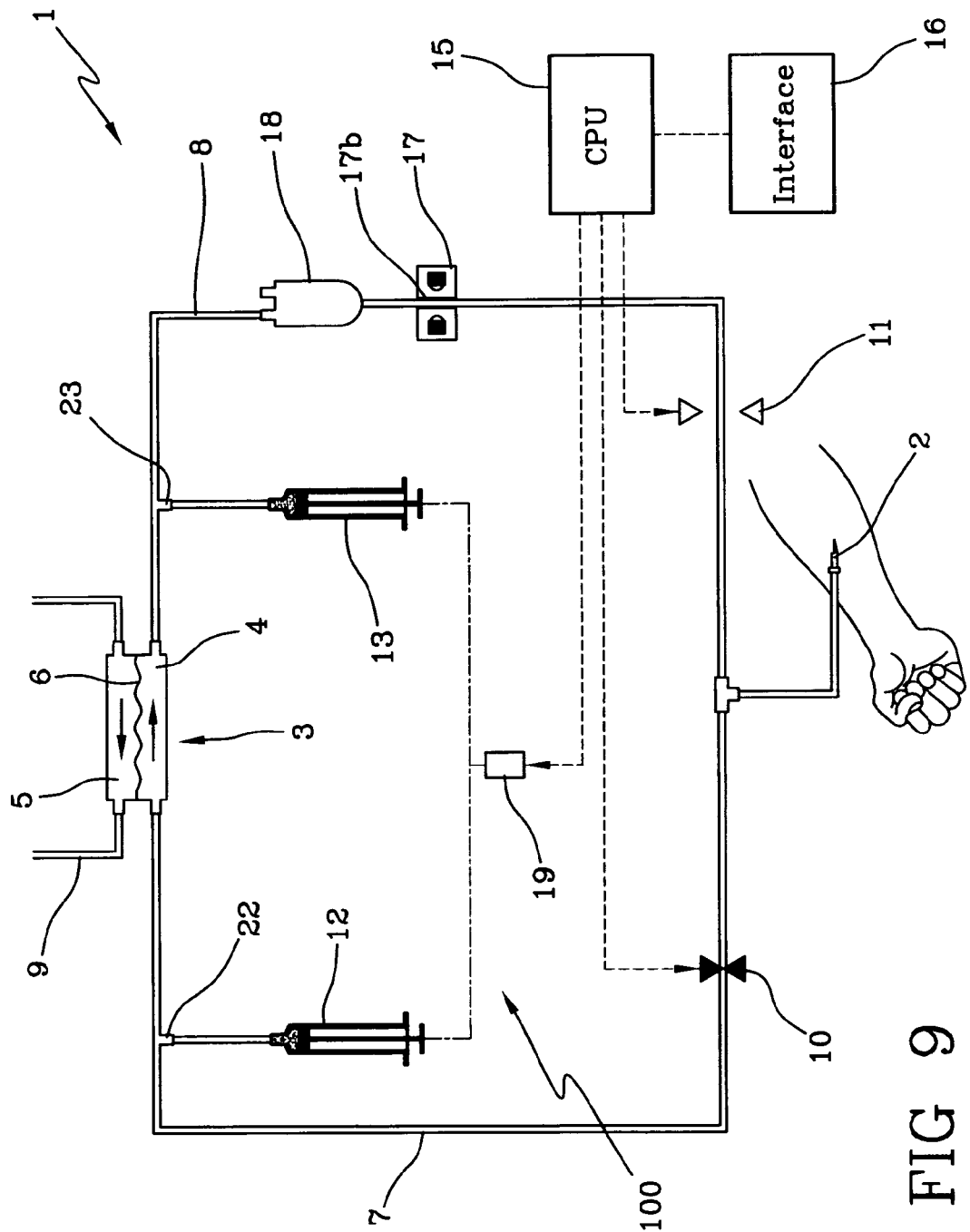
FIG. 9 represents a second embodiment with two chambers in a schematized way.

Furthermore, a second embodiment (FIG. 9) relates to the same device with a second chamber 13 which is in fluid communication with the extracorporeal blood circuit and defines a second additional blood volume, the said second chamber 13 having a variable total content making it possible to store blood during the arterial phase and release blood during the venous phase, this chamber 13 being rigid and including at least one wall capable of being moved. More particularly, the second chamber 13 may be in fluid communication with the return line 8 when the first chamber is in fluid communication with the intake line 7.

Figure 10:
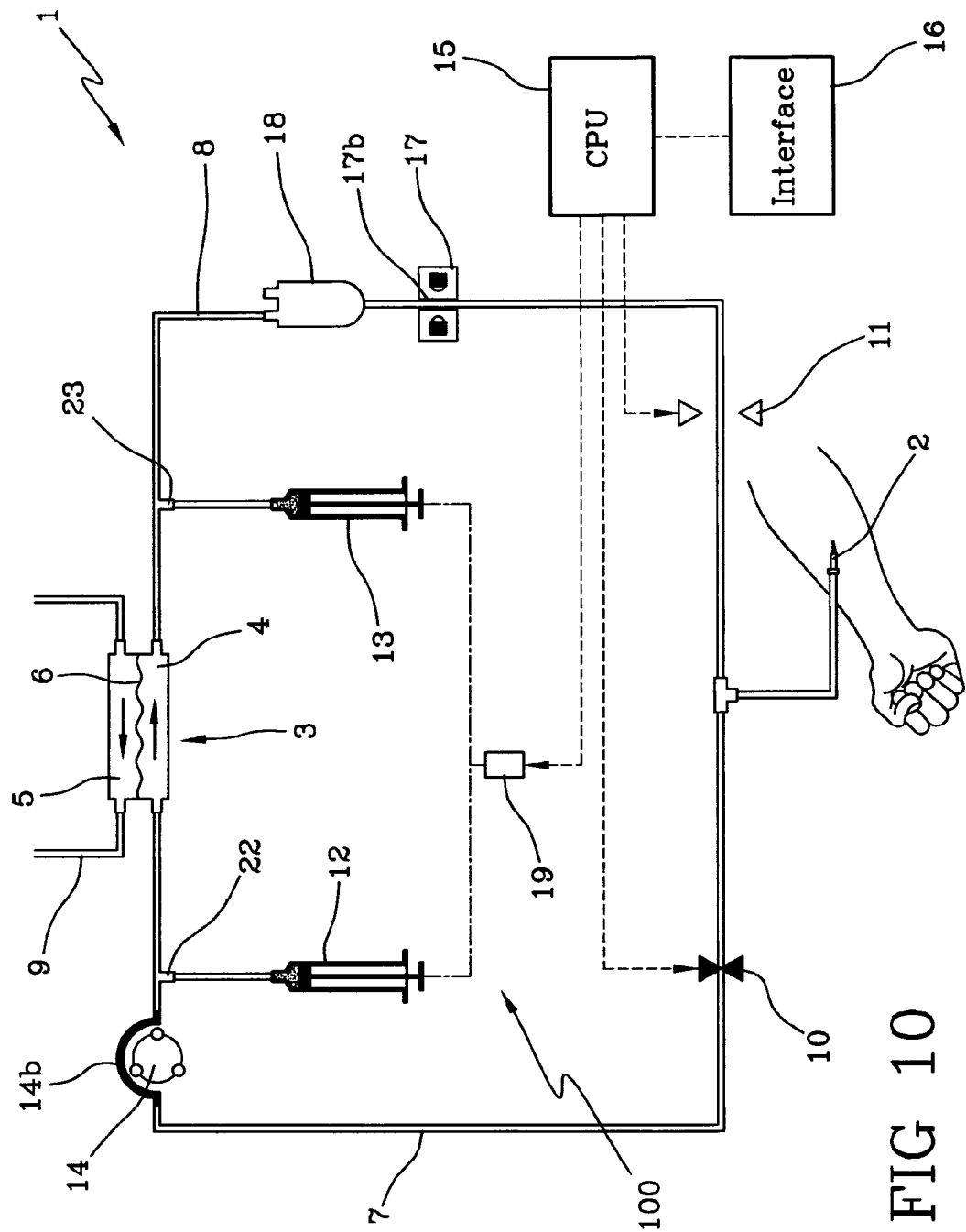
FIGS. 10 and 11 represent in a schematized way a third and a fourth embodiment with two chambers and a flow-rate regulating means (arbitrarily designed pump) positioned differently.
Figure 11:
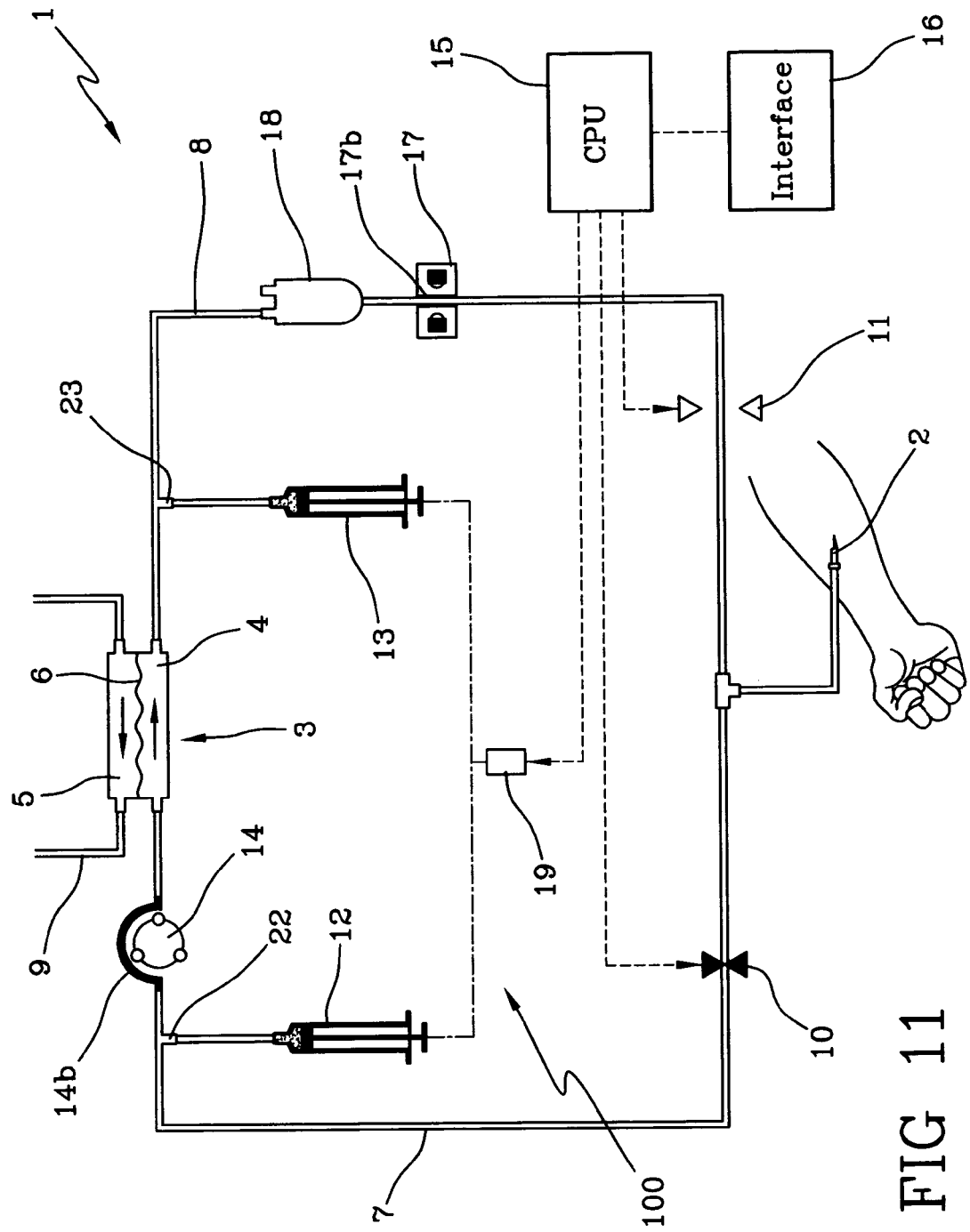
Figure 12:
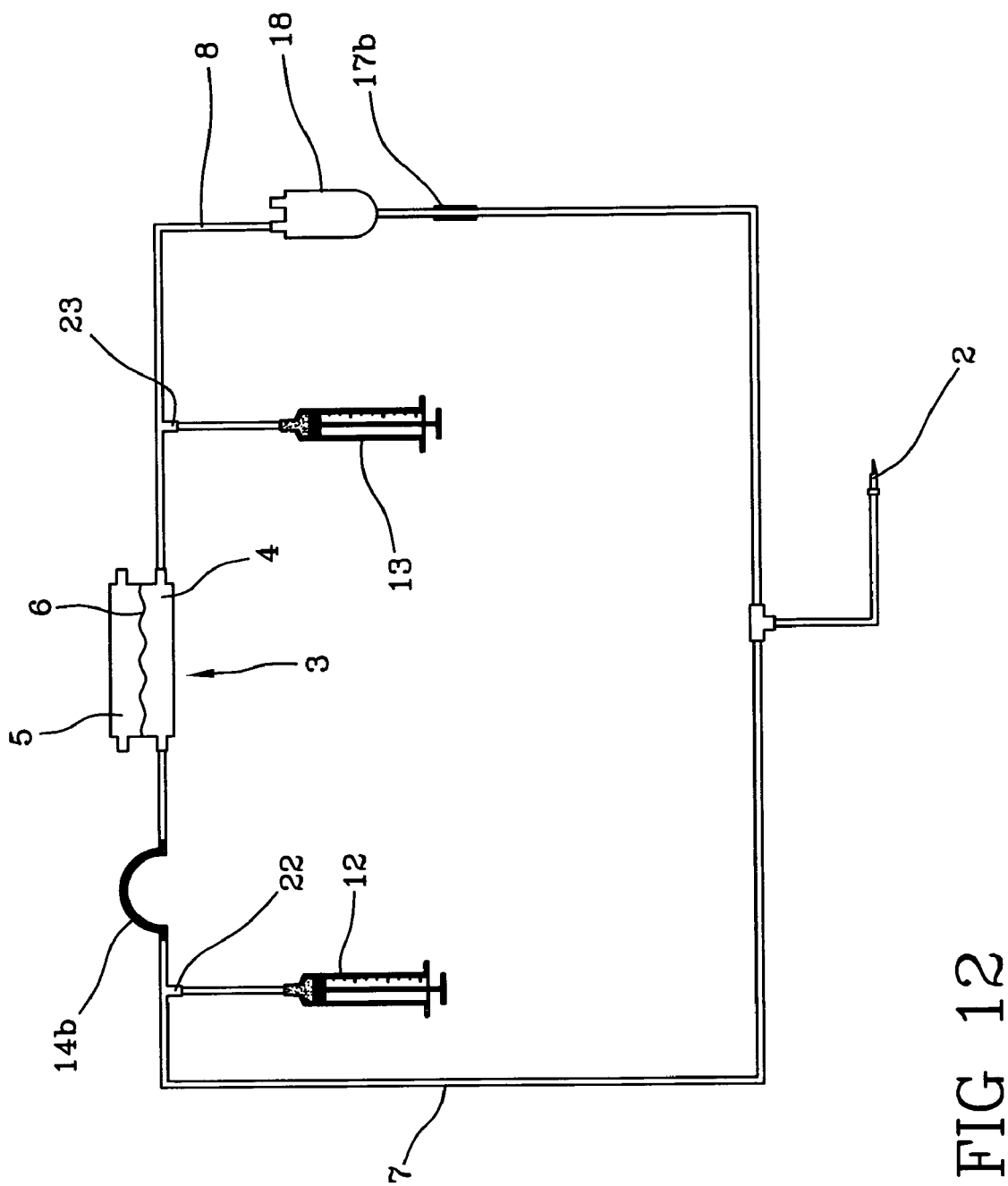
FIG. 12 represents the disposable device corresponding to the fourth embodiment.

A fluid flow-rate regulating means 14 may be present and act on the extracorporeal blood circuit. This fluid flow-rate regulating means may include a pump, particularly a peristaltic pump. This pump 14 may act upstream of the first compartment 4 of the treatment unit. More particularly, this pump 14 acts upstream of the first chamber 12 (third embodiment, illustrated in FIG. 10) or downstream of the first chamber 12 (fourth embodiment, illustrated in FIG. 11).

As an alternative, this pump 14 may act downstream of the first compartment 4 of the treatment unit. In this case, this pump 14 or its equivalent would act either upstream or downstream of the second chamber 13.

The closure means (10, 11) may be a pump, a valve, an active clamp or a combination of these instruments. Two clamps have been represented arbitrarily in the 4 embodiments which are illustrated, the first clamp 11 referred to as the "arterial clamp" acting on the intake line or arterial line 7, and the second clamp 12 referred to as the "venous clamp" acting on the return line or venous line 8.

An air detector 17 may be placed upstream of the part of the venous closure means (10, 11) acting on the return line 8. A part 17b of the return line will be operational with the air detector.

An air separator 18 may be inserted into the device. It may be connected downstream of the chamber or chambers (12, 13) and the treatment unit 3. The air separator is advantageously connected upstream of the part of the closure means (10, 11) acting on the return line 8, and immediately upstream of the optional air detector 17. The air separator 18 may also receive the air detector 17 on its own structure.

The air separator (18) may include a bubble trap. An air separator may also be inserted into each chamber (12, 13).

At least one of the chambers may be a rigid chamber with at least one wall intended to slide in the chamber. More particularly, one of the chambers may be a syringe. Such a syringe is advantageously positioned vertically with the needle upwards. These characteristics are illustrated in the first four embodiments.

The syringe may furthermore include an extensible diaphragm impermeable to bacteria, or to blood, of which at least one part is attached to the plunger and another part is attached to a circumference of the barrel of the syringe, so that it forms a barrier between the blood contained in the syringe and the ambient air. This makes it possible, in particular, to prevent contamination of the blood by air if a drop of blood were to pass between the sliding mobile wall and the barrel of the syringe. The diaphragm could be formed by gauze, cotton, etc.

The elastic diaphragm 43 impermeable to bacteria connects a point of the plunger to a circumference of the barrel towards the outer part of the latter. The diaphragm may be in the form of a concertina, for example, which can expand when the syringe is empty and contract when the syringe is full.

Figure 15:
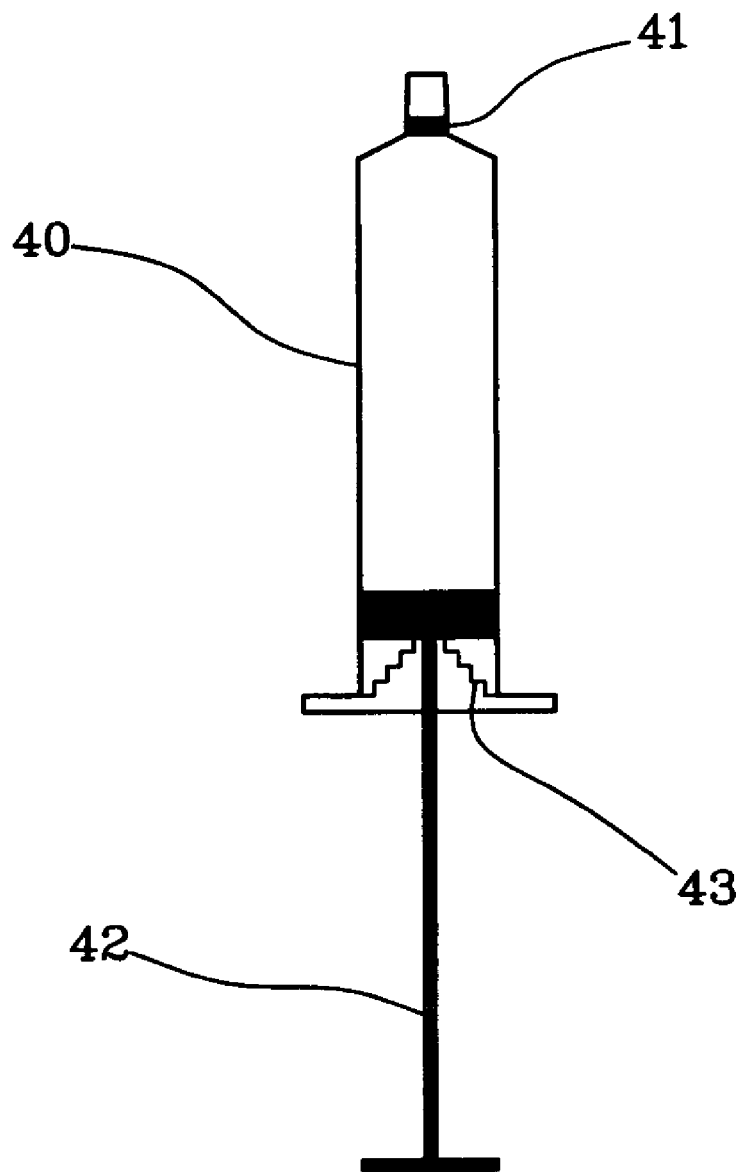
FIG. 15 represents a syringe which may be used in each embodiment.

At least one of the chambers (12, 13) may also include an opening to the outside, comprising a hydrophobic diaphragm (41) which is associated with the said opening and makes it possible to remove any undesirable air bubble present in the chamber (12, 13). This diaphragm may be placed as close as possible to the outlet of the syringe. It is represented at the top of the barrel 40 forming the syringe in FIG. 15, although it may be located anywhere on the chamber, on the mobile wall (plunger 42 in FIG. 15) or on the fixed wall.

In all the modes which are described, provision may be made for at least one chamber part (12, 13) to be transparent and include a scale for visual reading of the content. This allows the operator to immediately check the filling state of the chamber or chambers and to ascertain the "stroke volume" SV.

At least one chamber (12, 13) may be also be integrated inside the treatment unit 3.

The two chambers (12, 13) advantageously have the same structure and the same maximum content. Once the equipment has been regulated, this makes it possible to distribute the stroke volume into two identical volumes throughout operation.

A calculation and control unit (CPU) 15 is provided for simultaneously controlling the closure means (10, 11) in order to alternate the arterial phase and the venous phase, and controlling the filling of at least one of the two chambers (12, 13) during the arterial phase and the discharge of at least one of the two chambers (12, 13) during the venous phase.

The means 19 acting on the chambers (12, 13) in order to modify the volume of the chambers (12, 13) includes at least one actuation means for varying the volume of the chamber by moving at least one chamber wall. It will, for example, include a plunger.

The means 19 comprises a motor coupled with the actuation means. In the embodiment which includes two identical syringes, the motor will be coupled to the plunger of each syringe. The coupling will be such that the two plungers are actuated simultaneously and in the same position.

The CPU 15 comprises elements for controlling the means 19 acting on the chambers (12, 13) for modifying the volume of the chambers (12, 13) in order to fill at least one of the two chambers (12, 13) during the arterial phase, and to discharge at least one of the two chambers (12, 13) during the venous phase.

The CPU 15 comprises means for controlling the first fluid flow-rate regulating means 14 in order to ensure a substantially constant flow rate immediately downstream of the latter. This improves the quality of the blood treatment.

The CPU advantageously comprises means for controlling the means acting on the chambers (12, 13) for modifying the volume of the two chambers (12, 13) in order to set a volume in the first chamber 12 substantially equal to the volume in the second chamber 13 during operation of the device.

A user interface 16 is also provided, with means for receiving intended parameters, the CPU 15 comprising means for calculating control parameters from one or more planned machine parameters.

The device may also include:
a user interface 16 having means for receiving intended parameters;
measurement means for ascertaining measured parameters;
in which the calculation and control means 15 comprises means for calculating control parameters from one or more intended parameters and one or more measured parameters, and for controlling the device as a function of them.

The measurement means advantageously include pressure measurement means ($P_A$, $P_V$) for measuring the arterial pressure and the venous pressure. The arterial pressure may be measured upstream of the pump 14, and the venous pressure is the pressure at the outlet of the first compartment of the treatment unit (configuration in FIG. 13).

The measurement means may also include at least one flow meter (D1, D2) for ascertaining the ultrafiltration rate. A flow meter D1 may be provided on the fresh dialysate line and a flow meter D2 may be provided on the spent dialysate line, in order to ascertain the ultrafiltration rate, that is to say the flow rate of liquid extracted from the patient.

At least the intended stroke volume $SV_{int}$ figures among the intended parameters.

Operation of the Fourth Embodiment:

The operation of an embodiment will be described in more detail with reference to FIGS. 13 and 14.

Before the start of the treatment, the two syringes 12 and 13 are empty and are coupled with the actuation means 19 "driver". If the extracorporeal blood treatment device 1 is initially in a double-needle mode, the operator will be able to connect the disposable according to the invention onto the machine, unlock the syringes and tap the single needle 2 into the patient's blood access.

As soon as the treatment has started, the peristaltic pump 14 is primed, a first arterial phase is initiated by making the arterial clamp 10 open and the venous clamp 11 close, the blood passes through the needle and the intake line 7, fills the first syringe 12 and enters the first compartment 4 of the treatment unit 3, then the treated blood leaves the compartment 4, passes through the return line and fills the second syringe 13. Throughout the arterial phase, the blood is both stored and purified (in part) through the treatment unit.

Figure 13:
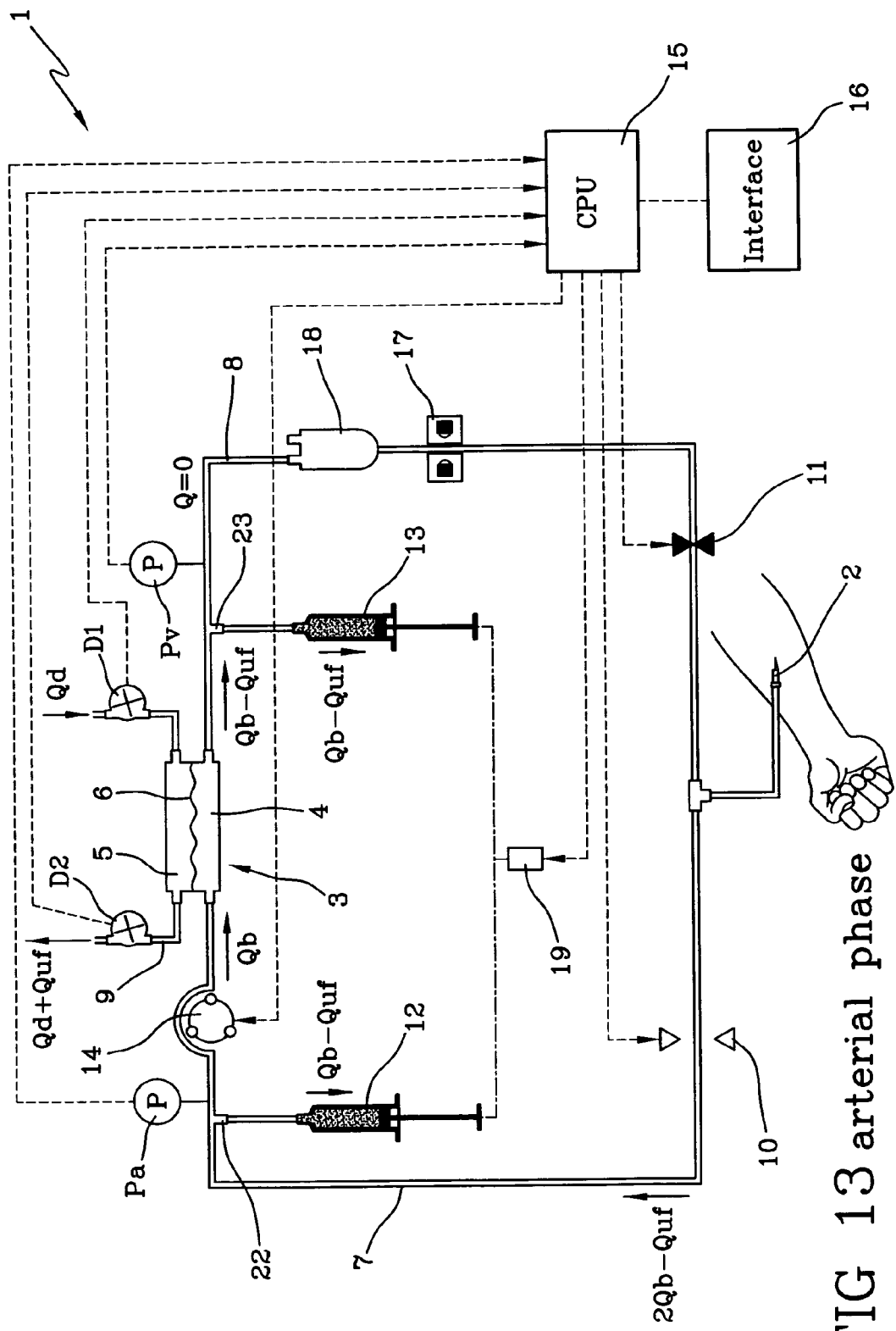
FIGS. 13 and 14 represent the operation of the device according to the fourth embodiment of the invention, respectively in an arterial phase and in a venous phase.
Figure 14:
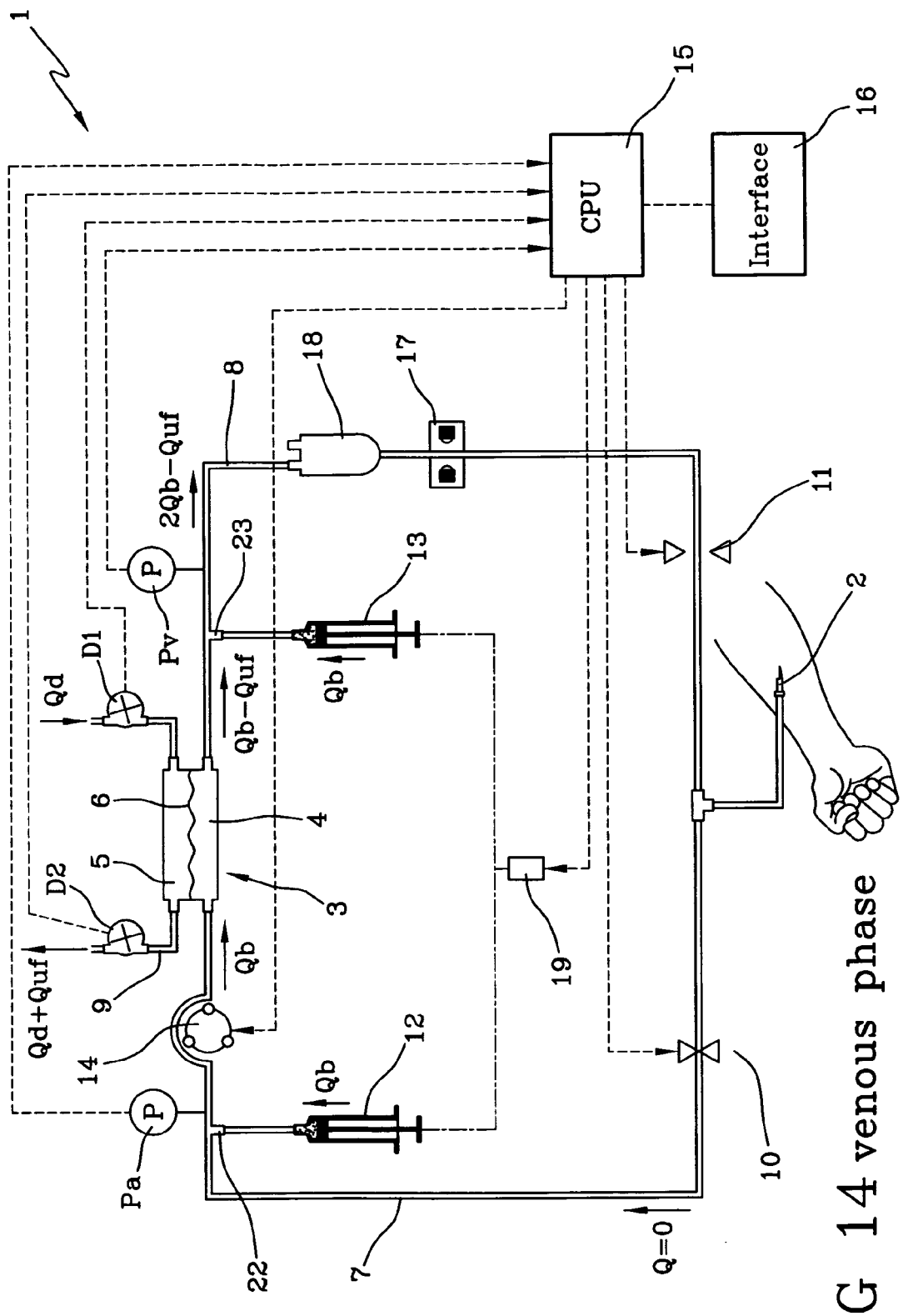

A budget of the flow rates can be determined easily, and this is reported on FIG. 13. $Q_B$ denotes the blood flow rate in the first compartment 4 of the treatment unit 3, $Q_D$ denotes the dialysate flow rate in the second compartment 5 and $Q_{UF}$ denotes the ultrafiltration rate of the patient's fluid taking place through the membrane 6, passing from the first compartment 5 to the second compartment 4. The blood flow rate downstream of the treatment unit is accordingly reduced by $Q_{UF}$.

In the embodiment being described, the chambers are syringes with the same structure and the same maximum content, equal to the stroke volume (SV) divided by 2. It will be recalled that the stroke volume SV is the maximum volume taken from the patient during one cycle (during the arterial phase and the venous phase). The arterial stroke volume $SV_A$ (respectively the venous stroke volume $SV_V$) denotes the maximum volume taken from the patient and pumped through the "arterial" first chamber 12 (respectively the "venous" second chamber 13). The following equations are therefore satisfied for this embodiment: $SV_A = SV_V = SV/2$.

Once the syringes have reached a predetermined filling threshold, the venous phase is then initiated by reverse control of the two clamps and return of the plungers of the syringes. The blood is accordingly released and returned to the patient.

In a First Possible Control Configuration of the Fourth Embodiment:

Besides the stroke volume SV, the intended parameters may include the intended blood flow rate $Q_{Bint}$ at the inlet of the first compartment 4.

The control parameters accordingly include at least the duration of the arterial phase $T_A$ and the duration of the venous phase $T_V$.

The budget of the flow rates in an arterial phase is illustrated in FIG. 13, and makes it possible to derive the control parameter:

$$T_A = \frac{Vsyringe}{(Qsyringe)} = \frac{SV}{2*(QBint - QUF)}$$

The following is likewise derived in a venous phase (see FIG. 14):

$$T_V = \frac{Vsyringe}{(Qsyringe)} = \frac{SV}{2*QBint}$$

As an alternative to choosing TA and TV, at least the actuation speed of the actuation means $V_{ACT}$ during the arterial phase, on the one hand, and during the venous phase, on the other hand, may be selected as control parameters.

This is because the actuation speed can be derived from the flow rate and the corresponding phase duration.

Measurement of the actuation time and the actuation speed of the syringes, or alternatively measurement of the volumes, or else the first of the two which pertains, may also be used as a reference for changing from one phase to another.

It should be recalled, however, that the chambers (12, 13) are airless chambers and behave somewhat like pumps.

The pressure on the circuit will therefore need to be regulated. To that end, the calculation and control unit includes means for regulating the blood flow rate $Q_B$ around the intended blood flow rate $Q_{Bint}$ as a function of the measured parameters $P_A$ and $P_V$.

This is because there may be a pressure "conflict" in an arterial phase between the venous chamber 13 and the pump 14 (due to flow rates which do not match, taking $Q_{UF}$ into account). It will accordingly be necessary to measure the venous pressure $P_V$ and regulate the blood flow rate $Q_B$ as a function of this measurement $P_V$ by substantial variation around $QB_{int}$: If $P_V$ decreases, then $Q_B$ will be substantially increased, and vice versa.

In a venous phase, there may likewise be a pressure "conflict" between the "arterial" chamber 12 and the pump 14 (due to flow rates which do not match, taking $Q_{UF}$ into account). It will accordingly be necessary to measure the venous pressure $P_A$ and regulate the blood flow rate $Q_B$ as a function of this measurement $P_A$ by substantial variation around $QB_{int}$: If $P_A$ decreases, then $Q_B$ will be substantially decreased, and vice versa.

This regulation makes it possible to refine the pressures $P_A$ and $P_V$ very effectively in order to maintain the haemodynamic conditions of constant pressure and flow rate.

In a Second Possible Control Configuration of the Fourth Embodiment:

Besides the stroke volume $SV_{int}$, the intended parameters may include the actuation speed $V_{ACTint}$ of the actuation means or, as an alternative to $V_{ACTint}$, the intended duration of the arterial phase $T_{Aint}$ and the intended duration of the venous phase $T_{Vint}$.

The control parameters accordingly include at least the blood flow rate $Q_B$.

The budget of the flow rates in an arterial phase is illustrated in FIG. 13, and makes it possible to derive the control parameter:

$$Q_{Bart} = QUF + \frac{SV}{2*TAint}$$

The following control parameter is likewise derived in a venous phase (see FIG. 14):

$$Q_{Bvei} = \frac{SV}{2*TVint}$$

In the same way as in the first control configuration, the pressure in the circuit will need to be regulated.

To that end, the calculation and control unit includes means for regulating the actuation speed $V_{ACT}$ around the intended actuation speed $V_{ACTint}$ as a function of the measured parameters $P_A$ and $P_V$. As an alternative, the calculation and control unit will include means for regulating the duration of the arterial phase $T_A$ around the intended duration of the arterial phase $T_{Aint}$ and for regulating the duration of the venous phase $T_V$ around the intended duration of the venous phase $T_{Vint}$, as a function of the measured parameters $P_A$ and $P_V$.

As an alternative, it will be possible to work either with the flow rate of the pump 14 or with the flow rate of the syringes (12, 13), or with both, in order to regulate the arterial pressure $P_A$ and the venous pressure $P_V$.

The calculation and control unit 15 is also intended to comprise means for controlling the following modes of operation: haemodialysis, haemofiltration, haemodiafiltration.

Figure 8:
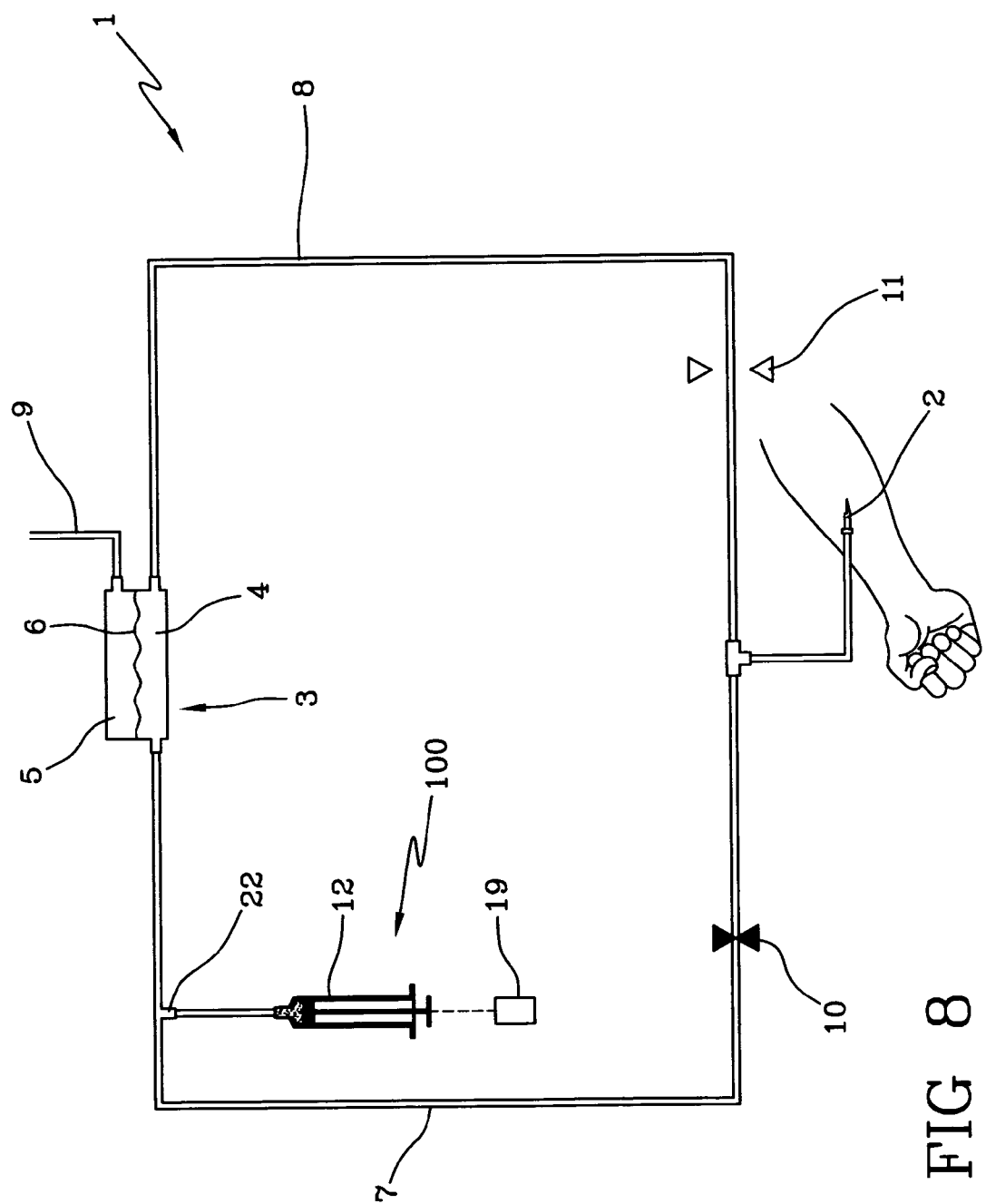

The invention also relates to the disposable device (or "disposable") 100 corresponding to the embodiments of the various instruments described above. The disposable device of the first embodiment, illustrated in FIG. 8, includes a treatment unit 3 having a first compartment 4 and a second compartment 5, which are separated by a semipermeable membrane 6; an extracorporeal blood circuit comprising a single needle 2, an intake line 7, the first compartment 4 of the treatment unit and a return line 8; at least a first chamber 12 for defining a first additional blood volume which includes a connection 22 in fluid communication with the intake line 7 or with the return line 8; the first chamber 12 having a variable total content and being rigid and including at least one wall capable of being moved. The first chamber 12 is advantageously in fluid communication with the intake line 7 via the said connection 22, which is fixed or removable. The disposable device of the fourth embodiment also includes a second chamber 13 for defining a second additional blood volume which includes a fixed or removable second connection 23 for placing the second chamber 13 in fluid communication with the return line 8, the second chamber 13 having a variable total content and being rigid and including at least one wall capable of being moved. The disposable device may include at least one part 14b capable of working with a flow-rate regulating means 14. This part 14b is placed on the intake line 7, downstream of the first connection 22. The disposable device may include a part 17b placed on the return line 8 and capable of working with an air detector 17. An air separator 18 may be connected onto the return line 8.

At least one of the chambers (12, 13) may be a rigid chamber with at least one wall intended to slide in the chamber, and will more particularly be a syringe. (The syringe may include an extensible diaphragm, which is impermeable to blood and of which at least one part is attached to the plunger and another part is attached to a circumference of the barrel of the syringe).

The syringe may moreover include an opening to the outside, comprising a hydrophobic diaphragm 41 which is associated with the said opening and makes it possible to remove any undesirable air bubble present in the chamber (12, 13). In all the modes, at least one part of the chamber or chambers (12, 13) may be transparent and include a scale for visual reading of the storage capacity.

At least one chamber (12, 13) may also be integrated inside the treatment unit 3.

The two storage means (12, 13) advantageously have the same structure and the same maximum content.

They may be placed side by side in order to facilitate their control by the actuation means. In the case of two syringes, they will be identical and placed side by side, and will have a common linear actuation means for the plungers.

The syringes may themselves be removable and fittable by virtue of two connectors 22 and 23 on the disposable device, which makes it possible to select and fit the syringes before the treatment, as a function of the intended stroke volume.

These controllable syringes with a variable total content are particularly advantageous because the storage of blood during single-needle operation obviates the use of the expansion chambers in the prior art. On the one hand, this obviation makes it possible to reduce coagulation owing to the absence of any air/blood interface, and makes it possible to avoid the compulsory presence of an air separator required downstream of the first chamber and upstream of the treatment unit. On the other hand, this obviation makes it possible to avoid having to ascertain and control the parameters of air pressure and air volume in the chambers. Indeed, level detectors or the like are no longer necessary for ascertaining the quantity of blood in the chamber: the position of the plunger or of the mobile partition of the chamber is easy to derive (from the maximum content and the position of the actuation means) and will give its instantaneous content. The syringes can furthermore be readily emptied again at the end of the venous phase, so that no blood will remain in the syringe, while maintaining accurate knowledge of the internal volume.

Placed side by side, the syringes furthermore fulfil the function of a pump and will make it possible to reduce the number of pumps needed in order to ensure a maximally constant, known and easily controllable blood flow rate. The flow rate of blood through the first compartment of the treatment unit is thus kept continuous and substantially constant.

The invention provides many advantages. It makes it possible:

To obtain improved biocompatibility owing to a limited risk of blood coagulation;
To change easily from a single-needle mode of operation to a double-needle mode of operation, and vice versa;
To see and ascertain the volume of blood by a visual assessment of the quantity of blood;
To reduce the extracorporeal volume of blood (stroke volume) to be treated,
To carry out easier integration of the machine,
To limit costs by the restricted use of pumps and storage means, and by the possibility of changing between the two modes, single-needle and double-needle;
to facilitate the procedure for the operator owing to a single connection.

The invention claimed is:

1. A device for extracorporeal treatment of blood intended to operate in a mode with a single needle, comprising:
a treatment unit having a first compartment and a second compartment, which are separated by a semipermeable membrane,
an extracorporeal blood circuit comprising a single needle, an intake line in fluid communication with the first compartment of the treatment unit, and a return line in fluid communication with the first compartment of the treatment unit,
a purge line at the outlet of the second compartment,
a closure means acting on at least the intake line and the return line in order to generate the alternate sequence of blood intake and return,
at least a first chamber in fluid communication with the extracorporeal blood circuit said first chamber defining a first additional blood volume, the first chamber having a variable total content;
wherein:
the first chamber is rigid and includes at least one movable wall,
the device includes a means acting on the first chamber in order to modify the volume of the first chamber, making it possible to store blood during the arterial phase and release blood during the venous phase, wherein the first chamber includes an opening to the outside, said opening having a hydrophobic diaphragm associated with said opening, said hydrophobic diaphragm being configured to remove any undesirable air bubble present in the first chamber.

2. A device according to claim 1, wherein the first chamber is in fluid communication with the intake line.

3. A device according to claim 2 further comprising a second chamber in fluid communication with the return line, said second chamber defining a second additional blood volume, said second chamber being rigid and including at least one wall capable of being moved; said second chamber further having a variable total content, such that blood is stored during an arterial phase and released during a venous phase.

4. A device according to claim 1 further comprising a fluid flow-rate regulating means acting on the extracorporeal blood circuit, said fluid flow-rate regulating means including a pump.

5. A device according to claim 4, wherein said fluid flow-rate regulating means acts upstream of the first compartment of the treatment unit.

6. A device according to claim 5, wherein said fluid flow-rate regulating means acts downstream of the first chamber.

7. A device according to claim 1 or 3 including at least one air detector placed upstream of a part of the closure means acting on the return line.

8. A device according to claim 1 or 3 further comprising at least one air separator.

9. A device according to claim 8, wherein the air separator is connected downstream of the first chamber and the treatment unit and immediately upstream of at least one air detector, said at least one air detector being placed upstream of a part of the closure means acting on the return line.

10. A device according to claim 1, wherein the first chamber is a rigid chamber with at least one wall intended to slide.

11. A device according to the claim 10, wherein at least one of the first and second chambers is a syringe.

12. A device according to the claim 11, wherein said at least one syringe includes a needle having an outlet, said at least one syringe being positioned vertically with the outlet of the needle facing upwards.

13. A device according to claim 11, wherein the syringe includes a plunger, a barrel, and an extensible diaphragm impermeable to bacteria, at least a part of said extensible diaphragm being attached to the plunger and another part of said extensible diaphragm being attached to a circumference of the barrel of the syringe.

14. A device according to claim 3 wherein the first and second chambers have the same structure and the same maximum content.

15. A device according to claim 3 further comprising a calculation and control unit for:
   simultaneously controlling the closure means in order to alternate the arterial phase and the venous phase, and
   controlling the filling of at least one of the first and second chambers during the arterial phase and the discharge of at least one of the first and second chambers during the venous phase.

16. A device according to the claim 15, further comprising a means acting on the second chamber in order to modify the volume of the second chamber wherein the means acting on the first and second chambers in order to modify the volume of the first and second chambers includes an actuation means for varying the volume of the first or second chamber or both the first and second chambers by moving at least one chamber wall, said actuation means including a plunger.

17. A device according to the claim 16, wherein the calculation and control unit comprises means for controlling the means acting on the first and second chambers to modify the volume of the first and second chambers in order to fill at least one of the first and second chambers during the arterial phase, and to discharge at least one of the first and second chambers during the venous phase.

18. A device according to claim 15, further comprising a fluid flow rate regulating means acting on the extracorporeal blood circuit, wherein the calculation and control unit comprises means for controlling the fluid flow-rate regulating means in order to ensure a substantially constant flow rate immediately downstream of the fluid flow-rate regulating means.

19. A device according to claim 16, wherein the calculation and control unit comprises means for controlling the means acting on the first and second chambers in order to set a volume in the first chamber substantially equal to the volume in the second chamber during operation of the device.

20. A device according to claim 15 further comprising:
   a user interface having means for receiving intended parameters;
   measurement means for ascertaining measured parameters;
   wherein the calculation and control means comprises means for calculating control parameters from one or more intended parameters and one or more measured parameters, and for controlling the device as a function of the one or more intended parameters and one or more measured parameters.

21. A device according to the claim 20, wherein the measurement means includes pressure measurement means for measuring the arterial pressure, $P_A$, and the venous pressure, $P_V$.

22. A device according to the claim 21, wherein the measurement means includes at least one flow meter for ascertaining the ultrafiltration rate.

23. A device according to claim 20, wherein the intended parameters include at least an intended stroke volume $SV_{int}$.

24. A device according to claim 20, wherein the intended parameters include an intended blood flow rate $Q_{Bint}$ at the inlet of the first compartment.

25. A device according to the claim 24, wherein the control parameters include at least a duration of the arterial phase $T_A$ and a duration of the venous phase $T_V$.

26. A device according to claim 24, wherein the control parameters include at least an actuation speed, $V_{ACT}$, of the actuation means.

27. A device according to claim 25 or 26, wherein the calculation and control unit includes means for regulating a blood flow rate $Q_B$ around the intended blood flow rate $Q_{Bint}$ as a function of measured parameters $P_A$ and $P_V$.

28. A device according to claim 20, wherein the intended parameters include an intended actuation speed, $V_{ACTint}$, of the actuation means.

29. A device according to claim 20, wherein the intended parameters include an intended duration of the arterial phase, $T_{Aint}$ and an intended duration of the venous phase $T_{Vint}$.

30. A device according to claim 28 or 29, wherein the control parameters include at least a blood flow rate $Q_B$.

31. A device according to claim 21, wherein the calculation and control unit includes means for regulating an actuation speed $V_{ACT}$ around an intended actuation speed $V_{ACTint}$ as a function of measured parameters $P_A$ and $P_V$.

32. A device according to claim 21, wherein the calculation and control unit includes means for regulating a duration of the arterial phase $T_A$ around an intended arterial phase duration $T_{Aint}$ and for regulating a duration of the venous phase $T_V$ around an intended venous phase duration $T_{Vint}$ as a function of measured parameters $P_A$ and $P_V$.

33. A device according to claim 3, wherein at least one of the first and second chambers is a rigid chamber with at least one wall intended to slide.

34. A device according to claim 3, wherein the second chamber includes an opening to the outside, said opening having a hydrophobic diaphragm associated with said opening, said hydrophobic diaphragm being configured to remove any undesirable air bubble present in the first chamber.

35. A device according to claim 9, wherein the air separator is connected downstream of the second chamber and the treatment unit, and is connected immediately upstream of at least one air detector, said at least one air detector being placed upstream of a part of the closure means acting on the return line.

* * * * *

UNITED STATES PATENT AND TRADEMARK OFFICE
CERTIFICATE OF CORRECTION

| | | |
|---|---|---|
| PATENT NO. | : 7,540,958 B2 | Page 1 of 1 |
| APPLICATION NO. | : 11/074067 | |
| DATED | : June 2, 2009 | |
| INVENTOR(S) | : Jacques Chevallet et al. | |

It is certified that error appears in the above-identified patent and that said Letters Patent is hereby corrected as shown below:

In claim 1, column 12, line 6, "circuit said" should read --circuit, said--.

In claim 11, column 12, line 52, "to the claim" should read --to claim--.

In claim 12, column 12, line 54, "to the claim" should read --to claim--.

In claim 16, column 13, line 10, "to the claim" should read --to claim--.

In claim 17, column 13, line 18, "to the claim" should read --to claim--.

In claim 18, column 13, line 26, "flow rate" should read --flow-rate--.

In claim 21, column 13, line 48, "to the claim" should read --to claim--.

In claim 22, column 14, line 1, "to the claim" should read --to claim--.

In claim 25, column 14, line 9, "to the claim" should read --to claim--.

Signed and Sealed this

Twenty-fifth Day of August, 2009

David J. Kappos
*Director of the United States Patent and Trademark Office*